United States Patent [19]

Hooven

[11] Patent Number: 4,557,721

[45] Date of Patent: Dec. 10, 1985

[54] SERVO VALVE

[75] Inventor: Michael D. Hooven, Miami, Fla.

[73] Assignee: Cordis Corporation, Miami, Fla.

[21] Appl. No.: 556,150

[22] Filed: Nov. 29, 1983

[51] Int. Cl.[4] .............................................. A61M 27/00
[52] U.S. Cl. ........................................ 604/9; 137/510;
604/247
[58] Field of Search .................... 604/9, 8, 247; 128/1;
137/508, 510

[56] References Cited

U.S. PATENT DOCUMENTS

| 3,756,243 | 9/1973 | Schulte ..................................... 604/9 |
| 3,768,508 | 10/1973 | Schulte ................................. 604/9 X |
| 3,769,982 | 11/1973 | Schulte .................................... 604/10 |
| 3,782,410 | 1/1974 | Stenby ............................. 137/588 X |
| 3,886,948 | 6/1975 | Hakim ....................................... 604/9 |
| 4,106,510 | 8/1978 | Hakim et al. ........................... 604/9 |
| 4,332,255 | 6/1982 | Hakim et al. ........................... 604/9 |

Primary Examiner—Stephen C. Pellegrino
Attorney, Agent, or Firm—Lockwood, Alex, FitzGibbon & Cummings

[57] ABSTRACT

An implantable valve for allowing the passage of cerebrospinal fluid (CSF) from a ventricle of the brain to a suitable drainage location in the body includes a movable diaphragm, one side of which is in pressure communication with the drainage location of the body and the other side of which is in pressure communication with the epidural spaces. A valve assembly, actuated by movement of the diaphragm in response to increased epidural pressure controls passage of CSF from the ventricles to the drainage area.

25 Claims, 8 Drawing Figures

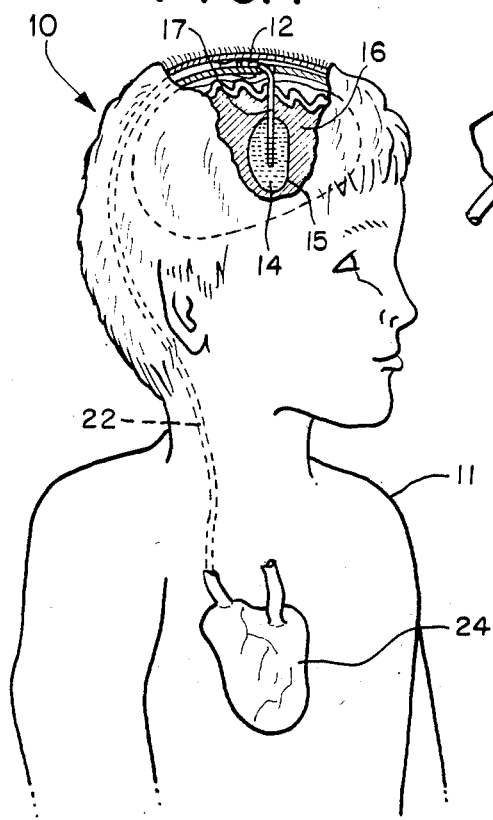
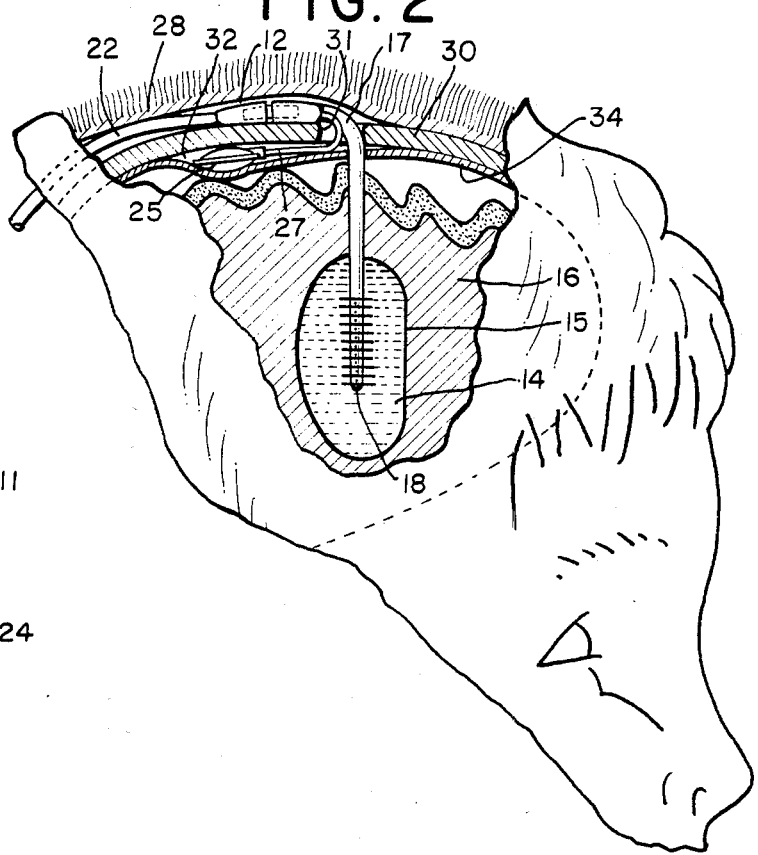
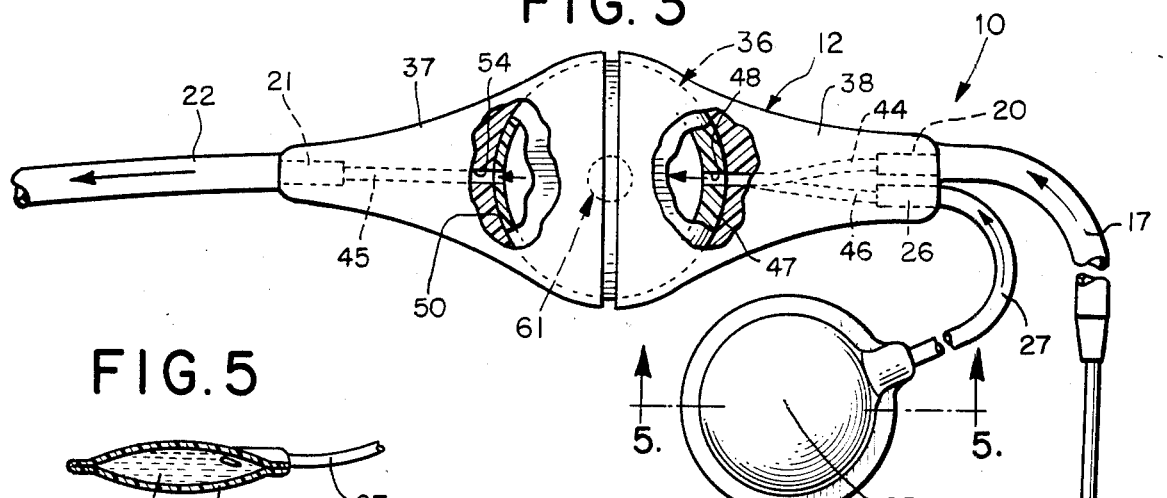
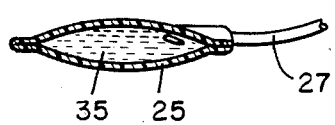
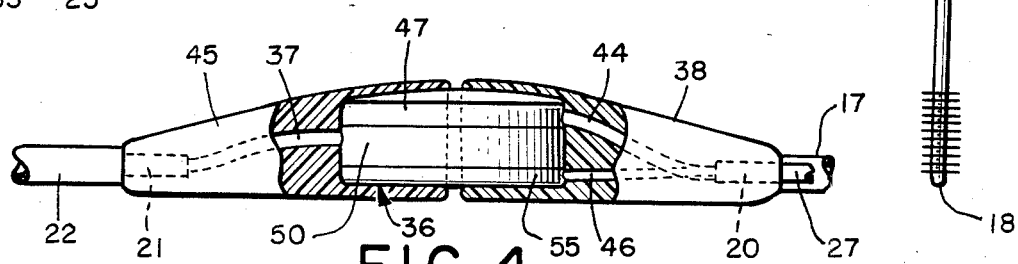

SERVO VALVE

BACKGROUND OF THE INVENTION

The present invention relates to an intracranial pressure relief valve and, more particularly, to a valve for shunting excess cerebrospinal fluid (CSF) from a ventricle in the brain to another location in the body of a patient when the epidural pressure reaches a predetermined magnitude.

Hydrocephalus is a condition in which the body, for any one of a variety of reasons, is unable to relieve itself of CSF which collects in the ventricles of the brain. The excessive collection of CSF in the ventricular spaces results in an increase of both epidural and intradural pressures. This in turn causes a number of adverse physiological effects including compression of brain tissue, impairment of blood flow in the brain tissue and impairment of the brain's normal metabolism.

Treatment of a hydrocephalic condition frequently involves relieving the abnormally high intracranial pressure. Accordingly, a variety of CSF pressure regulator valves and methods of controlling CSF pressure have been developed which include various forms of check valves, servo valves or combinations thereof. Generally, such valves serve to divert CSF from the ventricles of the brain through a discharge line to some suitable drainage area of the body, such as the venous system or the peritoneal cavity. Check valves operate by opening when CSF pressure exceeds pressure in the discharge line by a predetermined value.

Servo valves for use in the treatment of hydrocephalus typically allow drainage of CSF as needed to maintain a desired intracranial pressure as measured within the epidural or intradural spaces. A sensor responsive to pressure in such a space, establishes a pressure threshold which, when exceeded by the pressure in the epidural or intradural space results in opening of the valve to allow drainage of excess CSF. Preferably, the threshold so established is independent of ventricular CSF pressure.

For optimum performance, it is desirable that a servo valve have a high sensitivity to sensed pressure so that the desired intracranial pressure can be maintained with a high degree of accuracy. The present invention is directed to a servo valve which is extremely responsive to minute changes in the pressure of the fluids, thereby providing very accurate control of intracranial pressure. In this valve, the body fluids act on both sides of a movable area or diaphragm of relatively substantial surface area so that the valve is responsive to relatively small pressure differentials. Fluid in pressure communication with the discharge area of the body is applied to one side of the diaphragm while fluid in pressure communication with a sensor implanted in the epidural or intradural space is applied to the opposite side of the diaphragm. Relative movement of the diaphragm results in actuation of a valve assembly thereby controlling passage of CSF from the ventricular spaces to the selected discharge area within the body. As displacement of the diaphragm depends primarily on the difference between the sensor and discharge line pressures, a regulator valve having a threshold largely independent of ventricular CSF pressure is provided.

In view of the foregoing, it is a general object of the present invention to provide a new and improved pressure regulator valve for relieving intracranial pressure caused by the presence of excess CSF in the ventricles of the brain.

It is a more specific object of the present invention to provide a CSF pressure regulator valve which maintains a desired predetermined intracranial pressure.

It is still a more specific object of the present invention to provide a CSF pressure regulator valve which maintains a desired intracranial pressure independent of ventricular CSF pressure.

SUMMARY OF THE INVENTION

A valve for controlling the passage of body fluids from one location in the body to another location in accordance with an applied control pressure includes a housing having first, second and third interior chambers. First partition means in the housing separate the first and second chambers. Inlet port means are included for establishing fluid communication between the first chamber and the one location, while outlet port means establish fluid communication between the second chamber and the other location. The valve includes valving means between the first and second chambers which means are urged toward closing relationship by pressure in the first chamber when the pressure in the first chamber exceeds the pressure in the second chamber. Second partition means in the housing include a movable member separating the second and third chambers and are movable in response to the pressure differential therebetween. Sensing port means communicate the source of control fluid pressure with the third chamber, while means for coupling the movable member to the valving means cause the valving means to open when fluid pressure in the third chamber exceeds fluid pressure in the second chamber.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a perspective view, partially in section, of a hydrocephalus system employing a servo valve constructed in accordance with the invention, showing such a system implanted within a patient.

FIG. 2 is an enlarged perspective view of the implanted hydrocephalus system.

FIG. 3 is a plan view, partially in section of a hydrocephalus system showing the principal elements thereof.

FIG. 4 is a side elevational view, partially in section of a servo valve constructed in accordance with the invention.

FIG. 5 is a cross-sectional view of a pressure sensor bladder taken along line 5—5 of FIG. 3.

DESCRIPTION OF THE PREFERRED EMBODIMENT

Figure 6:
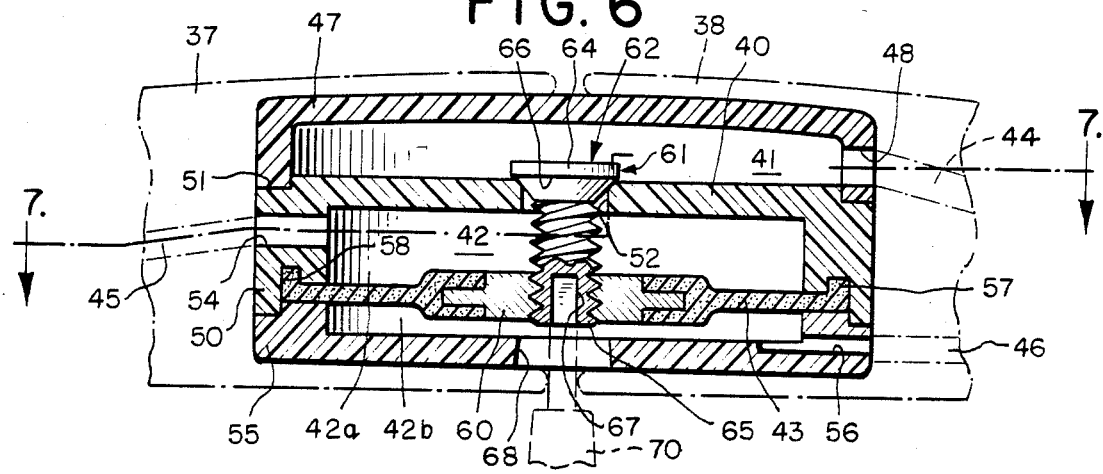
FIGS. 6 and 6a are side cross-sectional views of the valve of FIG. 4 illustrating the principal components and operation thereof.

Referring to the drawings, and particularly to FIGS. 1-3, a hydrocephalus system 10 for maintaining a desired predetermined intracranial pressure in a patient 11 is illustrated. The system shown includes a regulator servo valve 12 constructed in accordance with the present invention for maintaining the desired intracranial pressure.

Cerebrospinal fluid (CSF) 14 is drained from a ventricle 15 of the brain 16 by means of a ventricular catheter 17. Preferably, catheter 17 is radio-opaque thereby facilitating its accurate placement within the brain. The distal end 18 is provided with a plurality of apertures allowing the passage of CSF therethrough and is positioned in the brain ventricle in which the CSF accumulates, as illustrated. The other end of the catheter 17 is coupled to the input port 20 of the servo regulator valve 12, thereby establishing fluid communication between the valve and the ventricle. The discharge port 21 of the valve is attached to one end of a drain catheter 22, the opposite end of which discharges into an appropriate location of the patient's body. As illustrated, drain catheter 21 is threaded through an appropriate vein to terminate within the right atrium of the heart 24. When open, valve 12 allows passage of CSF from the ventricle of the brain to the selected discharge location thereby relieving CSF pressure caused by the excessive accumulation of the fluid within the ventricle 15.

In order to maintain a desired intracranial pressure the hydrocephalus system 10 includes means for sensing intracranial pressure. When the intracranial pressure exceeds a predetermined threshold, the valve opens, thereby allowing CSF to pass to the drainage area. Toward this end, the system includes a fluid filled pressure sensor bladder 25 connected to sensing port 26 of valve 12 by means of flexible conduit 27.

The details of the valve system implantation are best seen in FIG. 2. As indicated in the figure, the servo valve is generally flat thereby facilitating its implantation between the scalp 28 and the outer surface of the cranium 30. During implantation, a burr hole 31 is first provided in the skull. Next, the ventricular catheter 16 is inserted through the burr hole and into the ventricle 15. As further illustrated in FIG. 2, the pressure sensor bladder 25 is implanted within the epidural space 32 between the dura mater 34 and the interior surface of the cranium. Conduit 27 also passes through the burr hole to interconnect the sensor bladder with the servo valve. When thus installed, epidural pressure exerted on the sensor bladder is transmitted via conduit 27 and the fluid contained therein to the servo valve to control opening and closing of the valve.

Pressure sensor bladder 25 is generally disc-shaped in form as illustrated in FIGS. 3 and 5, is fashioned from a bio-compatible flexible material such as silicone rubber. The sensor fluid 35 contained within the bladder is incompressible and preferably bio-compatible in order to avoid adverse side effects in the event of leakage.

While the sensor as illustrated in FIG. 2 is implanted within the epidural space, it will be appreciated by those skilled in the art that an intradural implantation is possible and may be appropriate in some cases. As further illustrated in FIG. 2, drain catheter 22 is fully implanted beneath the scalp resulting in a completely implantable hydrocephalus system.

The internal construction and operation of servo regulator valve 12 may best be understood by reference to FIGS. 3-7. As indicated, the valve includes a disc-shaped inner housing 36 fashioned from a durable, biologically compatible material, such as thermo plastic polymers of polyethersulfone or polycarbonates. The inner housing 36 is received within an outer housing comprising two members 37 and 38 formed of silicone rubber on similar material bonded together over the inner housing. A partition 40 extending laterally across the interior portion of inner housing 36 divides the housing into first and second chambers 41 and 42, respectively. As illustrated, first coupling means in the form of a conduit 44 integrally formed in outer housing member 38 interconnect first chamber 41 with input port 20 thereby allowing CSF provided through ventricular catheter 17 to flow into the first chamber. Similarly, second coupling means in the form conduit 45 integrally formed in outer housing member 37 interconnect second chamber 42 with discharge port 21 thereby allowing fluid within the second chamber to discharge through the drain catheter. A flexible diaphragm 43 formed of silicone rubber or similar material lying substantially parallel to partition 40 traverses second chamber 42 thereby separating that chamber into upper and lower chambers 42a and 42b, respectively. Lower chamber 42b communicates with sensing port 26 by means of a third conduit 46 formed in outer housing member 38.

Figure 6A:
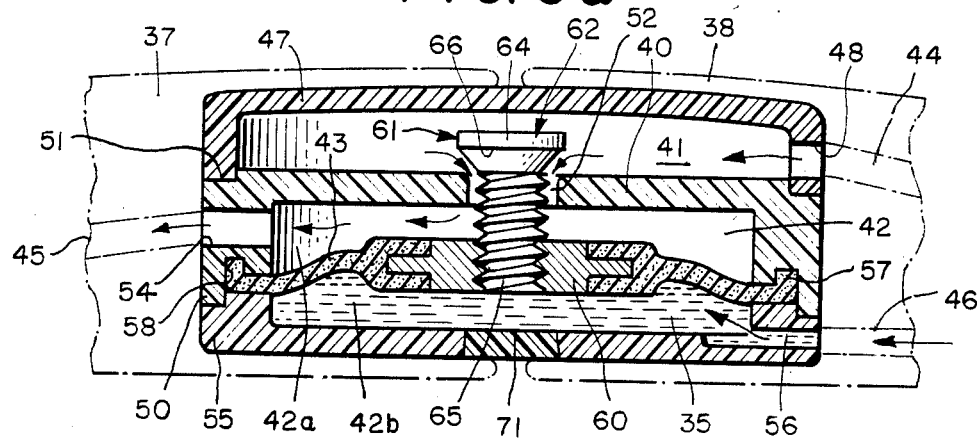
Figure 7:
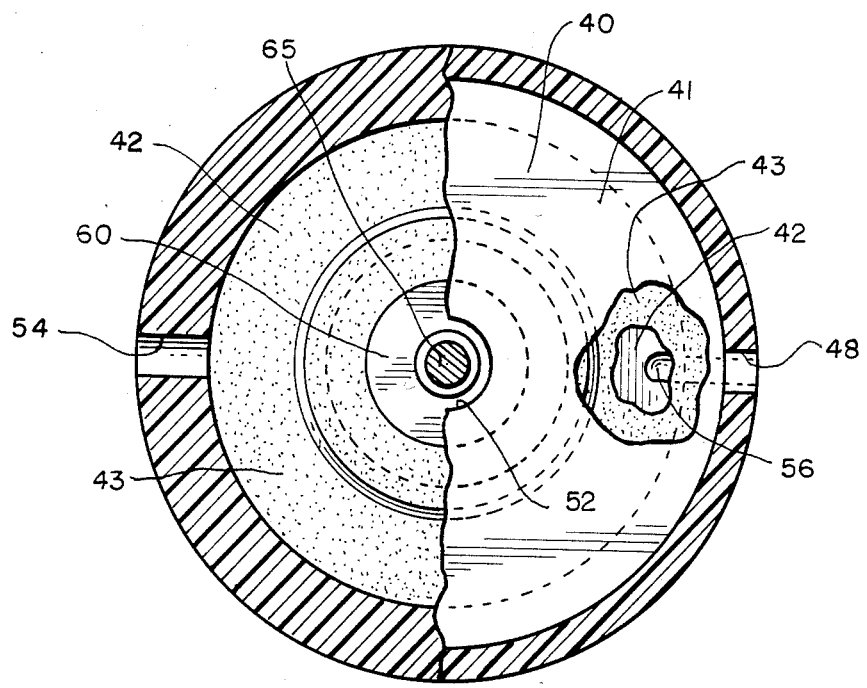
FIG. 7 is a cross-sectional view of the valve illustrated in FIG. 6 taken along line 7—7 thereof.

Referring to FIGS. 6 and 6a, the inner housing 36 is seen to include three interlocked disc-shaped members. Upper member 47 is cup-shaped and includes an aperture 48 for allowing the passage of CSF from conduit 44 therethrough. Intermediate member 50 is provided with an annular ledge 51 around the periphery of its upper surface for receiving the edge of upper member 47 allowing the members to interlock as shown. The upper surface of intermediate member 50 forms partition 40 and is provided with a centrally located aperture 52 therethrough. Another aperture 54 allows the passage of CSF through member 50 and into drain conduit 45. Lower member 55 interlocks with the lower edge of intermediate member 50 and includes aperture 56 for allowing sensor fluid to pass into lower chamber 42b. Diaphragm 43 includes an up-turned lip 57 received in a groove 58 formed in the lower edge of intermediate member 50 to lock the diaphragm between members 50 and 55. A nut 60, having an integrally threaded aperture located centrally therethrough is provided in a central location in diaphragm 43.

Fluid communication between chambers 41 and 42a, and hence between the ventricular and drain catheters is regulated by means of a valve assembly 61. Referring still to FIGS. 6 and 6a, valve assembly 61 includes valve seat means in partition 40 along the side forming an interior surface of chamber 41 and valve closure means in the form of valve stem 62. Valve stem 62, also formed of bio-compatible material, includes a portion of relatively larger diameter 64 and a portion of relatively narrow diameter 65 colinearly aligned with one another and interconnected by means of a ramped surface 66 as illustrated. In the embodiment shown, the valve seat means take the form of the aperture 52 centrally provided through the partition 40. The edge thus formed along the upper surface of the partition provides a seat against which the tapered surface 66 of valve stem 62 may rest to completely occlude aperture 52. As further indicated by the Figure, valve stem 62 is externally threaded along the length of its relatively narrow portion 65.

Because of the relationship between the valve stem and the diaphragm, displacement of the diaphragm, such as that resulting from differential pressure between chambers 42a and 42b results in vertical movement of the valve stem with respect to partition 40. By reference to FIG. 6, it will be observed that the inherent spring bias of diaphragm 43 pulls valve stem 62 downward until the ramped surface 66 thereof contacts the valve seat formed by aperture 52. The magnitude of this spring bias may be adjusted by rotating valve stem 62 relative to nut 60 thereby further engaging or disengaging the threads of each and effectively increasing or decreasing the height of the valve stem above the upper surface of the diaphragm. Thus, for example, by decreasing the height of valve stem 62 above diaphragm 43 (i.e. by engagingly rotating the valve stem) the diaphragm is caused to flex upwardly thereby increasing the tension on the valve stem and accordingly the pressure it exerts against its seat. To facilitate rotation of the valve stem, the stem is provided at its lower end with a square, axially aligned, keyway 67 accessible through an aperture 68 provided in the lower surface of inner housing 36 by means of which the valve stem may be rotated with a special tool 70 at the time of manufacture to provide a predetermined tension on the valve stem. Following such adjustment, a plug 71 is installed in aperture 68 to seal the unit.

Although the operation of the intracranial pressure servo regulator valve and method of the present invention should be clear from the foregoing description, a brief description of a preferred operation will be described.

The CSF in the ventricle 15 which is to be drained communicates with the valve via the ventricular catheter 17, conduit 44, and the first chamber 41. Fluid contained within pressure sensor bladder 25 communicates with the valve via the flexible conduit 27, sensing port 26, conduit 46 and chamber 42b. The pressure of this fluid, and hence the pressure exerted on the lower surface of diaphragm 43, is the epidural pressure exerted on pressure sensor bladder 25. The pressure exerted on the upper surface of diaphragm 43 will be that of the fluid discharge system. In the absence of a pressure differential between chambers 42a and 42b, the resilient nature of diaphragm 43 will cause it to tend to assume a substantially horizontal position as shown in FIG. 6. However, if the valve stem 62 is positioned such that it contacts the valve seat before the diaphragm can assume its favored position, the resulting pre-stressing of the diaphragm causes the diaphragm to exert a tension on the valve stem thereby preventing fluid communication between chambers 41 and 42a. Accordingly, CSF is precluded from passing through the valve to the discharge area of the body.

Ordinarily, a pressure differential exists between fluids in the discharge and sensing portions of the system. When the upwardly directed force on diaphragm 43 exerted by reason of the epidural pressure exerted on pressure sensor bladder 25 exceeds the downwardly directed force exerted on the diaphragm by reason of the discharge fluid pressure, the diaphragm is displaced upwardly thereby releasing the valve stem from its seat and allowing the passage of CSF from first chamber 41 to the discharge chamber 42a. In order to minimize the influence of CSF pressure on operation of valve stem 62, it is desirable to minimize the surface area of the upper portion of valve stem 62 exposed in chamber 41. If the surface area of diaphragm 43 greatly exceeds that of the exposed portion of the valve stem the additional force applied to the diaphragm by reason of an increase in CSF pressure in chamber 41 is insignificant compared with those forces exerted by reason of the fluids in chambers 42a and 42b. Accordingly, operation of the valve assembly is insignificantly affected by variations in CSF pressure existing in the ventricle being drained. It will be appreciated that if the drainage pressure exceeds the CSF pressure, the epidural pressure will never exceed the drainage pressure. Therefore, undesired back flow of fluid from chamber 42a to chamber 41 will never occur. Should drainage system pressure exceed both the CSF pressure and the epidural pressure, downward deflection of diaphragm 43 will result in valve stem 62 being urged to a closed position.

Because epidural pressure exceeds that of the drainage site selected, actuation of the valve assembly depends primarily on the pressure exerted in chamber 42b by reason of pressure on the sensor bladder 25. Accordingly, the servo regulator valve serves essentially to maintain a desired constant epidural pressure. Because of the relatively large surface area presented by the diaphragm, minor variations in epidural pressure will result in actuation of the valve assembly thereby maintaining the desired pressure within close limits. By way of example, the pressure regulator valve described herein is capable of accurate operation at CSF and epidural pressure differentials of 0–500 millimeters of water.

The pressure differential at which the valve opens may be adjusted as necessary for the patient. As previously developed this adjustment may be readily accomplished by threading up or down the valve stem to adjust the force by which its ramped surface bears against the valve seat. If the valve stem is threaded downwardly, it will preflex the diaphragm upwardly somwhat thereby resulting in a higher pressure differential which must be reached between chambers 42a and 42b before the valve stem moves away from its seat thereby allowing passage of CSF from chamber 41 to chamber 42.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A valve for controlling the passage of body fluids from one location in the body to another location in accordance with an applied control pressure, comprising:
   a housing having first, second and third interior chambers;
   first partition means in said housing separating said first and second chambers;
   inlet port means for establishing fluid communication between said first chamber and the one location;
   outlet port means for establishing fluid communication between said second chamber and the other location;
   valving means between said first chamber and said second chamber, said valving means being urged toward closing relationship by the pressure of fluid in said first chamber when said pressure in said first chamber exceeds fluid pressure in said second chamber;
   second partition means in said housing including a movable member separating said second and third chambers and movable in response to the pressure differential therebetween;

sensing port means opening into said third chamber for communicating said applied control pressure with said movable member; and means for coupling said movable member to said valving means whereby said valving means are opened against the pressure of the fluid in said first chamber when said control pressure in said third chamber exceeds fluid pressure in said second chamber.

2. A valve as defined in claim 1 wherein said movable member comprises a diaphragm which defines said second and third chambers.

3. A valve as defined in claim 2 wherein said valving means comprise an aperture through said first partition and a valve stem mounted for movement into closing relationship to said aperture.

4. A valve as defined in claim 3 wherein said coupling means comprise elongate means extending through said aperture and contacting said valving means to open said valving means against the pressure of the fluid in said first chamber.

5. A valve as defined in claim 4 wherein said valve stem is threaded for engaging a threaded aperture provided in said diaphragm.

6. A valve as defined in claim 5 further comprising a fluid filled pressure sensor bladder for developing said control pressure.

7. A valve for controlling the passage of body fluids from one location in the body to another location in accordance with a control pressure, comprising:

a housing having first, second and third interior chambers;

first partition means in said housing separating said first and second chambers;

inlet port means for establishing fluid communication between said first chamber and the one location;

outlet port means for establishing fluid communication between said second chamber and the other location;

valve seat means in said partition facing said first chamber, said valve seat means including an aperture through said partition for establishing fluid communication between said first chamber and said second chamber;

valve closure means positioned in said first chamber mounted for movement into closing relationship to said valve seat means;

second partition means in said housing including a movable member separating said second and third chambers and movable in response to the pressure differential therebetween;

sensing port means opening into said third chamber for communicating said control pressure with said movable member; and means for coupling said movable member to said valve closure means whereby said aperture is opened and closed in response to the pressure differentials between said second and third chambers.

8. A valve as defined in claim 7 wherein said movable member comprises a diaphragm which defines said second and third chambers.

9. A valve as defined in claim 8 wherein said coupling means comprise elongate means extending through said aperture and contacting said valve closure means to open said valve closure means against the pressure of the fluid in said first chamber.

10. A valve as defined in claim 9 wherein said coupling means and said valve closure means comprise a valve stem.

11. A valve as defined in claim 10 wherein said valve stem is threaded for engaging a threaded aperture provided in said diaphragm.

12. A valve as defined in claim 11 further comprising a fluid filled pressure sensor bladder for developing said control pressure.

13. An intracranial pressure relief valve for controlling the passage of cerebrospinal fluids from an intracranial source location in the body to a drainage location in accordance with an applied control pressure, comprising:

a housing having first, second and third interior chambers;

first partition means in said housing separating said first and second chambers;

inlet port means for establishing fluid communication between said first chamber and the intracranial source location;

outlet port means for establishing fluid communication between said second chamber and the drainage location;

valve seat means in said partition facing said first chamber, said valve seat means including an aperture through said partition for establishing fluid communication between said first chamber and said second chamber;

valve closure means positioned in said first chamber mounted for movement into closing relationship to said valve seat means;

second partition means in said housing including a movable member separating said second and third chambers and movable in response to the pressure differential therebetween;

sensing port means opening into said third chamber for communicating said control pressure with said movable member; and means for coupling said movable member to said valve closure means whereby said aperture is opened and closed in response to the pressure differential between said second and third chambers.

14. An intracranial pressure relief valve as defined in claim 13 wherein said movable member comprises a diaphragm which defines said second and third chambers.

15. An intracranial pressure relief valve as defined in claim 14 wherein said coupling means comprise elongate means extending through said aperture and contacting said valve closure means to open said valve closure means against the pressure of the fluid in said first chamber.

16. An intracranial pressure relief valve as defined in claim 15 wherein said coupling means and said valve closure means comprise a valve stem.

17. An intracranial pressure relief valve as defined in claim 16 wherein said valve stem is threaded for engaging a threaded aperture provided in said diaphragm.

18. An intracranial pressure relief valve as defined in claim 17 further comprising an epidurally located fluid filled pressure sensor bladder for developing said control pressure.

19. An intracranial pressure relief valve as defined in claim 17 further comprising an intradurally located fluid filled pressure sensor bladder for developing said control pressure.

20. A valve for controlling the passage of body fluid from a first location in the body to a second location so as to maintain a substantially constant predetermined pressure at a third location in the body, comprising:

a housing having a hollow interior;

first and second partition means in said housing dividing said hollow interior into first, second and third interior chambers, said second partition means including a movable member separating said second and third interior chambers;

inlet port means opening into said first interior chamber for admitting fluid from the first location into said first interior chamber;

outlet port means opening into said second interior chamber for discharging fluid from said second interior chamber to the second location;

sensing means for developing in said third chamber a control pressure indicative of pressure at the third location in the body;

valve seat means in said first partition facing said first chamber, said valve seat means including an aperture through said first partition for communicating fluid from said first interior chamber to said second interior chamber, said movable member moving in response to the pressure differential between said control pressure and the pressure of fluid in said second interior chamber; and valve closure means positioned in said first interior chamber coupled to said movable member for movement into closing relationship to said valve seat means whereby said aperture is opened and closed in response to the pressure differential between fluid in said second interior chamber and said control pressure.

21. A valve as defined in claim 20, wherein said movable means comprise a diaphragm separating said second and third interior chambers.

22. A valve as defined in claim 21, wherein said sensing means comprise a fluid filled pressure sensor bladder.

23. A valve as defined in claim 22, wherein said pressure sensor bladder is adapted for positioning in the epidural space of a patient.

24. A valve as defined in claim 23, wherein said valve is adapted to control the passage of cerebrospinal fluid from the ventricular spaces in a patient's brain to a drainage location in a patient's body.

25. A valve as defined in claim 24, wherein said valve closure means open and close said valve seat means so as to maintain said control pressure substantially constant.

* * * * *